United States Patent
Choi et al.

(10) Patent No.: US 11,517,223 B2
(45) Date of Patent: Dec. 6, 2022

(54) APPARATUS AND METHOD FOR ESTIMATING BLOOD GLUCOSE

(71) Applicant: SAMSUNG ELECTRONICS CO., LTD., Suwon-si (KR)

(72) Inventors: Ka Ram Choi, Hwaseong-si (KR); Sang Kon Bae, Seongnam-si (KR); So Young Lee, Daejeon (KR); Seung Keun Yoon, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 183 days.

(21) Appl. No.: 16/506,656

(22) Filed: Jul. 9, 2019

(65) Prior Publication Data

US 2020/0187835 A1    Jun. 18, 2020

(30) Foreign Application Priority Data

Dec. 13, 2018   (KR) .................. 10-2018-0160917

(51) Int. Cl.
*A61B 5/145*   (2006.01)
*A61B 5/024*   (2006.01)
(Continued)

(52) U.S. Cl.
CPC ...... *A61B 5/14532* (2013.01); *A61B 5/02125* (2013.01); *A61B 5/02416* (2013.01);
(Continued)

(58) Field of Classification Search
CPC ..... A61B 5/742; A61B 5/7235; A61B 5/0059; A61B 5/746; A61B 5/7455; A61B 5/7405;
(Continued)

(56) References Cited

U.S. PATENT DOCUMENTS 6,990,364 B2   1/2006   Ruchti et al.
9,554,738 B1 *  1/2017   Gulati ................. A61B 5/0075
(Continued)

FOREIGN PATENT DOCUMENTS

CN    106343979 A    1/2017
JP    2009-39267 A   2/2009
(Continued)

OTHER PUBLICATIONS

Communication dated Feb. 6, 2020 issued by the European Patent Office in counterpart European Patent Application No. 19185145.0.
(Continued)

*Primary Examiner* — Tse W Chen
*Assistant Examiner* — Avery M Foley
(74) *Attorney, Agent, or Firm* — Sughrue Mion, PLLC

(57) ABSTRACT

An apparatus for estimating blood glucose using a photoplethysmography (PPG) signal is provided. The apparatus for estimating blood glucose includes: a pulse wave sensor configured to obtain a pulse wave signal from an object; and a processor configured to obtain at least two points from a waveform of the pulse wave signal, to extract a feature based on time values of the obtained at least two points, and to estimate blood glucose based on the extracted feature.

20 Claims, 11 Drawing Sheets

(51) Int. Cl.
*A61B 5/00* (2006.01)
*A61B 5/021* (2006.01)
*A61B 5/0205* (2006.01)
*A61B 5/1455* (2006.01)

(52) U.S. Cl.
CPC ............ *A61B 5/681* (2013.01); *A61B 5/7278* (2013.01); *A61B 5/02055* (2013.01); *A61B 5/02116* (2013.01); *A61B 5/1455* (2013.01); *A61B 5/14546* (2013.01); *A61B 5/7246* (2013.01)

(58) Field of Classification Search
CPC . A61B 5/6803; A61B 5/4866; A61B 5/02405; A61B 5/021; A61B 5/0205; A61B 5/02007; A61B 5/7246; A61B 5/1455; A61B 5/14546; A61B 5/02116; A61B 5/02055; A61B 5/7275; A61B 5/7282; A61B 5/7278; A61B 5/681; A61B 5/02416; A61B 5/02108; A61B 5/14532
See application file for complete search history.

(56) References Cited

U.S. PATENT DOCUMENTS

| | | | |
|---|---|---|---|
| 2002/0198443 A1* | 12/2002 | Ting | A61B 5/02116 600/323 |
| 2010/0036221 A1 | 2/2010 | Lee et al. | |
| 2012/0059267 A1* | 3/2012 | Lamego | A61B 5/022 600/483 |
| 2013/0332085 A1* | 12/2013 | Yang | G01N 27/416 702/22 |
| 2014/0276556 A1 | 9/2014 | Saint et al. | |
| 2016/0157733 A1* | 6/2016 | Gil | A61B 5/14551 600/301 |
| 2017/0079533 A1* | 3/2017 | Robinson | A61B 5/0075 |
| 2017/0143279 A1* | 5/2017 | Jayaraman | A61B 5/4842 |
| 2017/0245767 A1* | 8/2017 | Ferber | A61B 5/0285 |
| 2018/0008200 A1* | 1/2018 | Romesburg | A61B 5/7253 |
| 2018/0116571 A1* | 5/2018 | Ajima | A61B 5/00 |
| 2019/0011467 A1* | 1/2019 | Shimizu | A61B 5/1495 |
| 2021/0401332 A1* | 12/2021 | John | A61B 5/02116 |

FOREIGN PATENT DOCUMENTS

| | | |
|---|---|---|
| JP | 2014-147637 A | 8/2014 |
| KR | 10-2010-0022614 A | 3/2010 |
| KR | 10-2011-0094405 A | 8/2011 |
| KR | 10-2012-0043189 A | 5/2012 |
| KR | 10-1512076 B1 | 4/2015 |
| KR | 10-2016-0075230 A | 6/2016 |
| KR | 10-2019-0065090 A | 6/2019 |
| WO | 2015/167251 A1 | 11/2015 |
| WO | 2018/119663 A1 | 7/2018 |

OTHER PUBLICATIONS

Geng et al., "Noninvasive Continuous Glucose Monitoring Using a Multisensor-Based Glucometer and Time Series Analysis", Scientific Reports, Oct. 2017, pp. 1-10, 10 pages total.

Monte-Moreno, "Non-invasive estimate of blood glucose and blood pressure from a photoplethysmograph by means of machine learning techniques", Artificial Intelligence in Medicine, May 2011, pp. 127-138, 12 pages total.

Man et al., "Meal Simulation Model of the Glucose-Insulin System", IEEE Transactions on Biomedical Engineering, vol. 54, No. 10, Oct. 2007, pp. 1740-1749, 10 pages total.

* cited by examiner

APPARATUS AND METHOD FOR ESTIMATING BLOOD GLUCOSE

CROSS-REFERENCE TO RELATED APPLICATION(S)

This application claims priority from Korean Patent Application No. 10-2018-0160917, filed on Dec. 13, 2018, in the Korean Intellectual Property Office, the entire disclosure of which is herein incorporated by reference for all purposes.

BACKGROUND

1. Field

Apparatuses and methods consistent with example embodiments relate generally to an apparatus and a method for estimating blood glucose, and more particularly to technology for non-invasively estimating blood glucose using a pulse wave signal.

2. Description of the Related Art

Diabetes is a chronic disease that causes various complications and can be difficult to cure, such that people with diabetes are advised to regularly check their blood glucose to prevent complications. In particular, when insulin is administered to control blood glucose, the blood glucose levels have to be closely monitored to avoid hypoglycemia and control insulin dosage. An invasive method of finger pricking is generally used to measure blood glucose levels. However, while the invasive method may provide high reliability in measurement, it may cause pain and inconvenience as well as an increased risk of disease infections. Recently, research has been conducted to provide a method of non-invasively measuring blood glucose by using a spectrometer without blood sampling.

SUMMARY

One or more example embodiments provide an apparatus and a method for accurately estimating blood glucose in a non-invasive manner.

In an aspect of an example embodiment, there is provided an apparatus for estimating blood glucose, the apparatus including: a pulse wave sensor configured to obtain a pulse wave signal from an object; and a processor configured to obtain at least two points from a waveform of the pulse wave signal, to extract a feature based on time values of the obtained at least two points, and to estimate blood glucose based on the extracted feature.

The pulse wave sensor may include: at least one light source configured to emit light of at least one wavelength onto the object; and at least one detector configured to detect the light of at least one wavelength scattered or reflected from the object.

The at least one wavelength may include at least one of a red wavelength, a green wavelength, a blue wavelength, and an infrared wavelength.

The processor may obtain a first point in a systolic interval of the pulse wave signal, and a second point in a diastolic interval of the pulse wave signal.

The processor may extract, as the feature, at least one of a difference between a time value of the first point and a time value of the second point, and a time difference ratio obtained by dividing the difference by the time value of the first point or the time value of the second point.

The processor may obtain a component of a pulse waveform forming the waveform of the pulse wave signal, and may obtain the first point and the second point based on the obtained component of the pulse waveform.

The processor may detect a local minimum point from a waveform of a differential signal, obtained by performing differentiation on the pulse wave signal, and may obtain at least one of a time value and a signal strength of the detected local minimum point as the component of the pulse waveform.

The feature may further include at least one of pulse rate variability, heart rate variability, heart rate, pulse rate, arterial stiffness, blood pressure, perfusion index, and pulsatile volume.

The processor may estimate the blood glucose by applying a blood glucose estimation model to the extracted feature.

In addition, the apparatus for estimating blood glucose may further include an output interface configured to provide a processing result of the processor to a user.

In another aspect of an example embodiment, there is provided a method of estimating blood glucose, the method including: obtaining a pulse wave signal from an object; obtaining at least two points from the pulse wave signal; extracting a feature based on time values of the obtained at least two points; and estimating blood glucose based on the extracted feature.

The obtaining of the at least two points may include obtaining a first point in a systolic interval of the pulse wave signal, and a second point in a diastolic interval of the pulse wave signal.

The extracting of the feature may include extracting, as the feature, at least one of a difference between a time value of the first point and a time value of the second point, and a time difference ratio obtained by dividing the difference by the time value of the first point or the time value of the second point.

The obtaining of the at least two points may include obtaining a component of a pulse waveform forming a waveform of the pulse wave signal, and obtaining the first point and the second point based on the obtained component of the pulse waveform.

The obtaining of the at least two points may include detecting a local minimum point from a waveform of a differential signal, obtained by performing differentiation on the pulse wave signal, and obtaining at least one of a time value and a signal strength of the detected local minimum point as the component of the pulse waveform.

In yet another aspect of an example embodiment, there is provided an apparatus for estimating blood glucose, the apparatus including: a pulse wave sensor configured to obtain a pulse wave signal from an object; a metabolism information obtainer configured to obtain metabolism information of a user; and a processor configured to estimate a first blood glucose value based on a feature extracted from the pulse wave signal, to estimate a second blood glucose value based on the metabolism information, and to estimate a final blood glucose value based on the first blood glucose value and the second blood glucose value.

The processor may extract the feature based on time values of the at least two points of a waveform of the pulse wave signal.

The processor may obtain a first point in a systolic interval of the waveform of the pulse wave signal, and a second point in a diastolic interval of the waveform of the pulse wave signal; and may extract, as the feature, at least one of a difference between a time value of the first point and a time value of the second point, and a time difference ratio obtained by dividing the difference by the time value of the first point or the time value of the second point.

The processor may obtain a component of a pulse waveform forming the waveform of the pulse wave signal, and may obtain the first point and the second point based on the obtained component of the pulse waveform.

The metabolism information obtainer may obtain the metabolism information based on at least one of sensor information, received from at least one of the pulse wave sensor, a food intake sensor, and a blood glucose sensor, and user input information.

The metabolism information obtainer may obtain the metabolism information by applying at least one of the sensor information and the user input information to a metabolism model.

The metabolism information may include at least one of a blood glucose change rate over time, a blood glucose variation, and a probability or a frequency of stages of blood glucose change stages.

The processor may estimate the second blood glucose value based on a calibration blood glucose value obtained by a blood glucose sensor, and the metabolism information.

The processor may estimate the final blood glucose value by applying a blood glucose estimation model to the first blood glucose value and the second blood glucose value.

The blood glucose estimation model may be predefined based on at least one of weighted summation, Kalman Filter, regression, and Artificial Intelligence.

In still another general aspect, there is provided a method of estimating blood glucose, the method including: obtaining a pulse wave signal from an object; obtaining metabolism information of a user; extracting a feature from the pulse wave signal; estimating a first blood glucose value based on the extracted feature; estimating a second blood glucose value based on the metabolism information; and estimating a final blood glucose value based on the first blood glucose value and the second blood glucose value.

The extracting of the feature may include: obtaining a first point in a systolic interval of the waveform of the pulse wave signal, and a second point in a diastolic interval of the waveform of the pulse wave signal; and extracting, as the feature, at least one of a difference between a time value of the first point and a time value of the second point, and a time difference ratio obtained by dividing the difference by the time value of the first point or the time value of the second point.

The obtaining of the metabolism information may include obtaining the metabolism information based on at least one of sensor information, received from at least one of the pulse wave sensor, a food intake sensor, and a blood glucose sensor, and user input information.

The obtaining of the metabolism information may include obtaining the metabolism information by applying at least one of the sensor information and the user input information to a metabolism model.

The estimating of the final blood glucose value may include estimating the final blood glucose value by applying a blood glucose estimation model to the first blood glucose value and the second blood glucose value.

BRIEF DESCRIPTION OF THE DRAWINGS

The above and/or other aspects will be more apparent by describing certain example embodiments with reference to the accompanying drawings, in which.

DETAILED DESCRIPTION

Figure 1A:
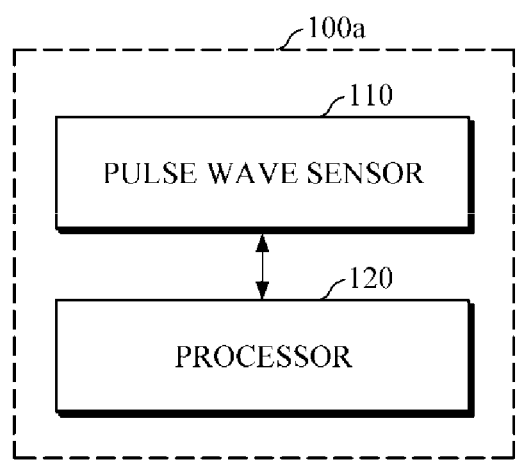
FIGS. 1A and 1B are block diagrams illustrating an apparatus for estimating blood glucose according to example embodiments.

Details of example embodiments are included in the following detailed description and drawings. Aspects of example embodiments will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Figure 1B:
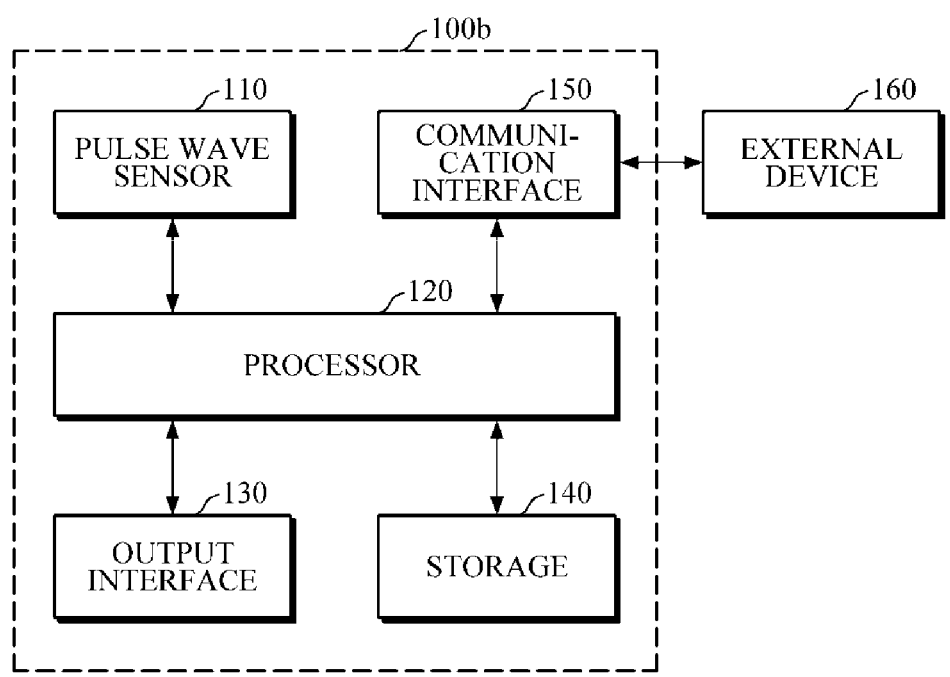
Figure 2A:
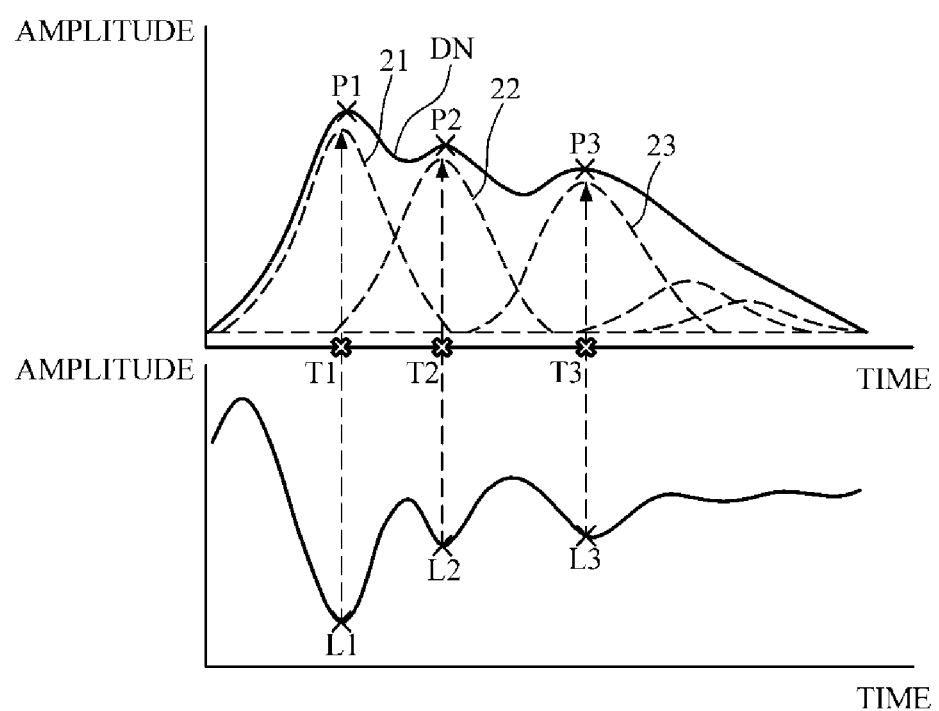
FIGS. 2A, 2B, and 2C are diagrams explaining examples of extracting features for estimating blood glucose.
Figure 2B:
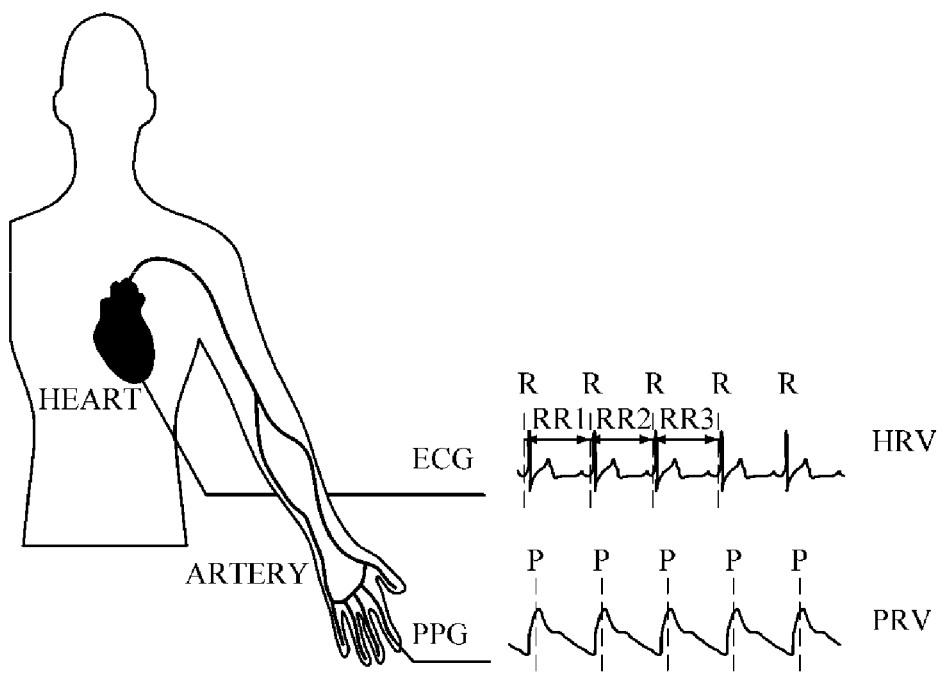
Figure 2C:
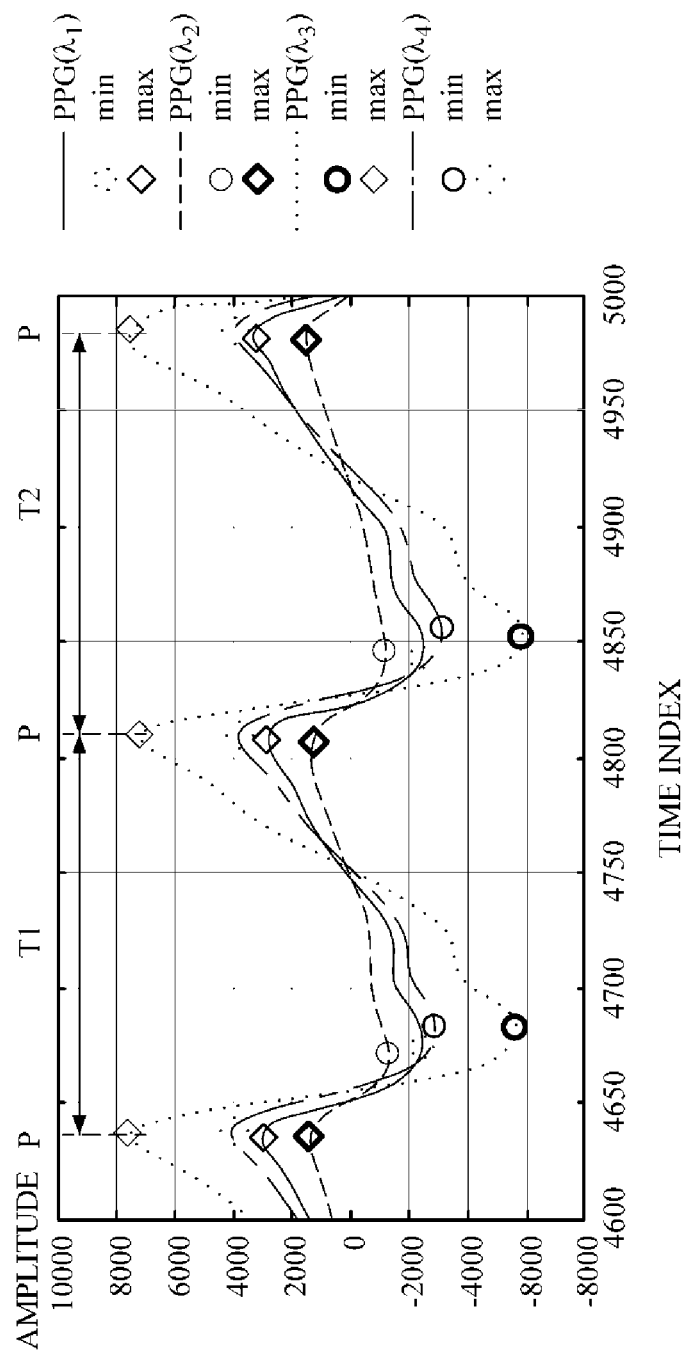

FIGS. 1A and 1B are block diagrams illustrating an apparatus for estimating blood glucose according to example embodiments. FIGS. 2A to 2C are diagrams explaining examples of extracting features for estimating blood glucose.

A blood glucose estimating apparatus 100a shown in FIG. 1A and a blood glucose estimating apparatus 100b shown in FIG. 1B according to example embodiments may be embedded in an electronic device, such as a smartphone, a tablet personal computer (PC), a desktop computer, a laptop computer, and the like, or in a medical device of a specialized medical institution. Alternatively, the blood glucose estimating apparatuses 100a and 100b may be manufactured as an independent device, such as a wearable device including a wristwatch-type wearable device, a bracelet-type wearable device, a wristband-type wearable device, a ring-type wearable device, a glasses-type wearable device, a headband-type wearable device, and the like, which may be worn on an object.

Referring to FIGS. 1A and 1B, the blood glucose estimating apparatuses 100a and 100b include a pulse wave sensor 110 and a processor 120.

The pulse wave sensor 110 may measure a pulse wave signal, including a photoplethysmography (PPG) signal, from an object. The pulse wave sensor 110 may include: a light source which emits light onto the object; and a detector which detects scattered or reflected light when light, emitted by the light source, is scattered or reflected from a body tissue of the object such as the surface of skin or blood vessels.

The light source may emit light of one or more different wavelengths onto the object. For example, different wavelengths may include a blue wavelength, a green wavelength, a red wavelength, an infrared wavelength, and the like, but are not limited thereto. The light source may include at least one of a light emitting diode (LED), a laser diode (LD), a fluorescent body, and the like, but is not limited thereto. One or more light sources may be positioned at different distances from the detector.

The detector may include one or more pixels which detect light, scattered or reflected from body tissues of the object, and convert the detected light into an electric signal. The one or more pixels may include a photo diode, a photo transistor (PTr), an image sensor (e.g., CMOS image sensor), and the like, but are not limited thereto.

The processor 120 may receive a pulse wave signal from the pulse wave sensor 110, and may extract features for estimating blood glucose based on the received pulse wave signal.

For example, the processor 120 may obtain two or more points from a waveform of the pulse wave signal, and may extract features for estimating blood glucose based on amplitude information and/or time information of the obtained two or more points. In this case, the processor 120 may obtain a point from each of a systolic interval and a diastolic interval of the waveform of the pulse wave signal. For example, the processor 120 may obtain a peak of the systolic interval and a peak of the diastolic interval as points for extracting features. Here, the systolic interval may refer to an interval from a starting point of the pulse wave signal to a dicrotic notch (DN) point, and the diastolic interval may refer to an interval after the dicrotic notch point of the pulse wave signal.

Referring to FIG. 2A, the upper diagram illustrates a pulse wave signal measured by the pulse wave sensor 110. As illustrated in FIG. 2A, a waveform of the pulse wave signal may be composed of a plurality of pulse waveforms 21, 22, and 23. Generally, the pulse wave signal is a superposition of a propagation wave 21, starting from the heart toward the distal end portions of the body, and reflection waves 22 and 23 reflected from the distal end portions or a branching point of the blood vessel and returning back therefrom.

The processor 120 may obtain two or more points based on components of pulse waveforms forming the pulse wave signal, e.g., time and/or amplitude (or signal strength) values. For example, among the pulse waveforms forming the pulse wave signal, the processor 120 may obtain a first point P1 based on a component of the first pulse waveform 21 which is associated with a propagation wave appearing in the systolic interval before DN. Further, of the pulse waveforms 22 and 23 appearing in the diastolic interval after DN, the processor 120 may obtain a second point P2 based on a component of the second pulse waveform 22 having the highest amplitude among the pulse waveforms forming the pulse wave signal.

The bottom diagram of FIG. 2A illustrates a waveform of a differential signal obtained by performing second order differentiation on a pulse wave signal. Referring to the bottom diagram of FIG. 2A, the processor 120 may perform second order differentiation on a pulse wave signal, and may obtain components of pulse waveforms, forming the pulse wave signal, based on the waveform of the second order differential signal. For example, the processor 120 may detect local minimum points from the waveform of the second order differential signal, and may obtain components of constituent pulse waveforms based on the detected local minimum points L1, L2, and L3. In this case, the local minimum point refers to a point at which a downward convex shape is formed, in an interval of a second order differential signal which is observed to be decreased and then is increased again past a specific point.

For example, the processor 120 may obtain a pulse wave signal point P1, corresponding to a first local minimum point L1 of the second order differential signal, as the first point associated with the first pulse waveform, and may obtain a pulse wave signal point P2, corresponding to a second local minimum point L2 of the second order differential signal, as the second point associated with the second pulse waveform.

As described above, the processor 120 may extract features for estimating blood glucose based on a time value T1 of the first point P1 and a time value T2 of the second point P2, which are obtained from the pulse wave signal. For example, the processor 120 may extract, as the feature, a difference (T2−T1) between the time value T1 of the first point P1 and the time value T2 of the second point P2. Alternatively, the processor 120 may extract, as the feature, a time difference ratio (T2−T1)/T1 obtained by dividing the difference (T2−T1) between the time value T1 of the first point P1 and the time value T2 of the second point P2 by the time value T1 of the first point P1, or a percentage of the time difference ratio. However, determination of the features in example embodiments are not limited thereto.

In another example, the processor 120 may extract various other types of information as features for estimating blood pressure. For example, the processor 120 may further obtain, as the features, pulse rate variability, heart rate variability, heart rate, pulse rate, arterial stiffness, blood pressure, perfusion index, pulsatile volume, and the like. However, the features are not limited thereto, and the processor 120 may extract various features based on various bio-signals obtained from a user using various sensors mounted in the blood glucose estimating apparatuses 100a and 100b or in an external device.

The processor 120 may obtain features for estimating blood glucose by combining the obtained information items. For example, referring to FIGS. 2B and 2C, the processor 120 may estimate pulse rate variability (PRV) by analyzing NN intervals T1 and T2 of the pulse wave signal of multiple wavelengths $\lambda_1$, $\lambda_2$, $\lambda_3$, and $\lambda_4$ measured from a user.

Upon obtaining the features for estimating blood glucose based on the pulse wave signal, the processor 120 may estimate blood glucose by applying a predefined blood glucose estimating model. In this case, the blood glucose estimating model may be defined as a linear/non-linear mathematical function which indicates a correlation between the obtained feature value and a blood glucose value. The following Equation 1 is an example of a simple linear function, but is not limited thereto.

$$y_1 = ax_1 + b \quad \text{[Equation 1]}$$

Herein, $x_1$ denotes the obtained feature value, $y_1$ denotes a blood glucose value to be obtained, and a and b are values pre-calculated through preprocessing.

Referring to FIG. 1B, the blood glucose estimating apparatus 100b according to an example embodiment includes an output interface 130, a storage 140, and a communication interface 150.

The output interface 130 may output a processing result of the processor 120 to a user. For example, the output interface 130 may visually output an estimated blood glucose value by using a display module (e.g., a display device). Alternatively, the output interface 130 may output the value in a non-visual manner through voice, vibrations, tactile sensation, and the like by using a speaker module (e.g., a speaker), a haptic module (e.g., a vibration motor), and the like. The output interface 130 may divide a display area into two or more areas according to a setting, in which the output interface 130 may output a pulse wave signal graph, a blood glucose estimation result, and the like, which are used for estimating blood glucose, in a first area; and may output a blood glucose estimation history in the form of graphs and the like in a second area. In this case, when an estimated blood glucose value falls outside a normal range, the output interface 130 may output warning information in various manners, such as highlighting an abnormal value in red and the like, displaying the abnormal value along with a normal range, outputting a voice warning message, adjusting a vibration intensity, and the like.

The processor 120 may generate various health-related information items based on the blood glucose estimation result, and may output the generated information through the output interface 130. For example, in response to a blood glucose estimation result being lower than a predetermined threshold (e.g., 70 mg/dL), the processor 120 may diagnose hypoglycemia, and may provide health-related information including an action to be made by a user, or a change in dosage of medication to be taken by a user.

In addition, the processor 120 may generate various health indices by tracking blood glucose estimation results during a predetermined period of time stored in the storage 140, and may provide the health indices to a user through the output interface 130.

For example, the processor 120 may generate a stress score indicating a blood glucose score or a blood glucose metabolism level. For example, the processor 120 may calculate a hypoglycemia/hyperglycemia frequency and/or a stress frequency by dividing a number of times of hypoglycemia/hyperglycemia and/or a number of times of stress during a predetermined period of time by a total number of data. Further, the processor 120 may calculate a period of hypoglycemia/hyperglycemia and/or a stress period by dividing a time of hypoglycemia/hyperglycemia and/or a stress time during a predetermined period of time by a total data time. In another example, along with or separately from the calculation, the processor 120 may generate analysis information associated with a maximum glucose value and a minimum glucose value in a day during a predetermined period of time, and/or information on a change in blood glucose and physiological responses, and the like. However, the information is merely an example, and the processor 120 may generate various other health indices.

In this case, the output interface 130 may output a blood glucose score and/or a stress score in the first area of the display, and may output the analysis information associated with a maximum glucose value and a minimum glucose value in a day during a predetermined period of time in the second area of the display. Alternatively, the output interface 130 may output a blood glucose score or a stress score in the first area of the display, and may output information on a change in blood glucose and physiological responses in the second area of the display. However, this is merely exemplary, and the output interface 130 may output one information item in the entire area of the display. In addition, while outputting two information items in each area of the display, when a user selects any one information item, the output interface 130 may output the selected information in the entire area of the display by enlarging the information.

The storage 140 may store a processing result of the processor 120. Further, the storage 140 may store various types of reference information required for estimating blood glucose. For example, the reference information may include user characteristic information such as a user's age, sex, health condition, and the like. In addition, the reference information may include a reference blood glucose value, a blood glucose estimation model, a blood glucose estimation interval, and the like, but is not limited thereto.

In this case, the storage 140 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 150 may communicate with an external device 160 using wired and/or wireless communication techniques under the control of the processor 120, to transmit and receive various data. For example, the communication interface 150 may transmit a blood glucose estimation result to the external device 160. Further, the communication interface 150 may receive various types of reference information required for estimating blood glucose from the external device 160. For example, the communication interface 150 may receive a reference blood glucose value and the like from an external device for measuring blood glucose which is an invasive/minimally invasive/non-invasive device. In this case, examples of the external device 160 may include an external device for measuring blood glucose which is an invasive/minimally invasive/non-invasive device, and an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 3:
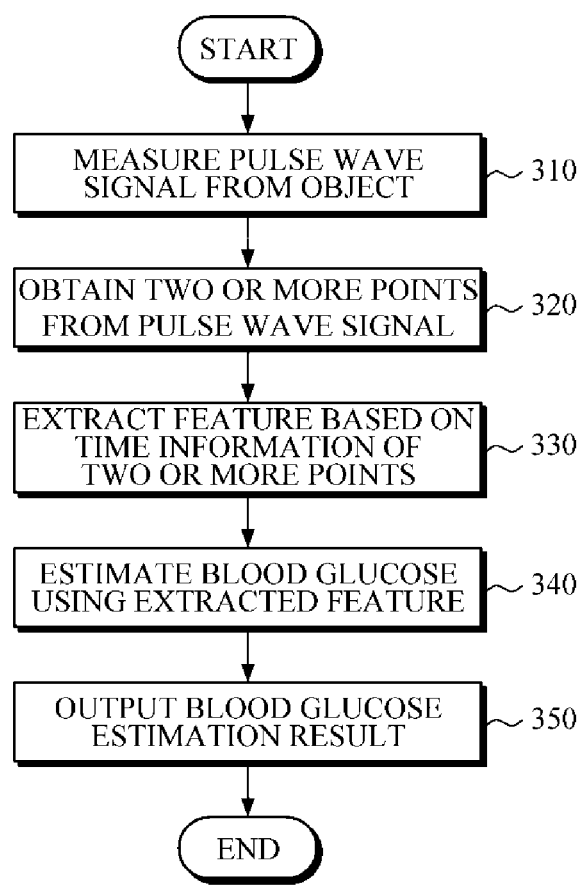
FIG. 3 is a flowchart illustrating a method of estimating blood glucose according to an example embodiment.

FIG. 3 is a flowchart illustrating a method of estimating blood glucose according to an example embodiment. The blood glucose estimating method of FIG. 3 may be performed by the blood glucose estimating apparatuses 100a and 100b according to embodiments of FIGS. 1A and 1B, which will be briefly described below in order to avoid redundancy.

In response to a request for estimating blood glucose, the blood glucose estimating apparatus may measure a pulse wave signal from an object in 310. In this case, the request for estimating blood glucose may be received from a user or an external device, or may be generated at predetermined blood glucose estimation intervals. The blood glucose estimating apparatus may include: one or more light sources which emit light onto an object to measure a pulse wave signal including a PPG signal; and a detector which detects light scattered or reflected from the object.

The blood glucose estimating apparatus may obtain two or more points from the pulse wave signal to extract features for estimating blood glucose in 320. For example, the blood glucose estimating apparatus may obtain a peak of the systolic interval and a peak of the diastolic interval as points for extracting features. For example, the blood glucose estimating apparatus may obtain the peak of the systolic interval and the peak of the diastolic interval based on components of pulse waveforms forming the pulse wave signal. In this case, the blood glucose estimating apparatus may detect local minimum points from a second order differential signal, obtained by performing second order differentiation on the pulse wave signal, and may obtain a time value and an amplitude value of each local minimum point as components of each pulse waveform. In other words, the blood glucose estimating apparatus may obtain, as a point of the systolic interval, a pulse wave signal point corresponding to a first pulse waveform component associated with a propagation wave of the second order differential signal, i.e., corresponding to a time value of a first local minimum point. Likewise, the blood glucose estimating apparatus may obtain, as a point of the diastolic interval, a pulse wave signal point corresponding to a second pulse waveform generally having the highest amplitude among the pulse waveform components associated with a reflection wave, i.e., corresponding to a time value of a second local minimum point.

Subsequently, the blood glucose estimating apparatus may extract features based on time information and/or amplitude information obtained at two or more points of the pulse wave signal in 330. For example, the blood glucose estimating apparatus may extract, as the feature, a difference between a time value obtained in the diastolic interval and a time value obtained in the systolic interval. In another example, the blood glucose estimating apparatus may extract, as the feature, a time difference ratio obtained by dividing the difference between the time value of the diastolic interval and the time value of the systolic interval by the time value of the systolic interval, or a percentage of the time difference ratio. However, the features are not limited thereto, and the blood glucose estimating apparatus may further obtain information such as pulse rate variability, heart rate variability, heart rate, pulse rate, arterial stiffness, blood pressure, perfusion index, pulsatile volume, and the like, and may combine the obtained information items to obtain a new feature.

Next, upon extracting the features, the blood glucose estimating apparatus may estimate blood glucose by applying a blood glucose estimation model in 340. The blood glucose estimation model may be a linear/non-linear function which indicates a correlation between a feature value and a blood glucose value, but is not limited thereto.

The blood glucose estimating apparatus may output a blood glucose estimation result and may provide the result to a user in 350. For example, the blood glucose estimating apparatus may output the blood glucose estimation result by various visual methods using a visual output device such as a display and the like. Alternatively, the blood glucose estimating apparatus may output the blood glucose estimation result by non-visual methods through voice, tactile sensation, vibrations, and the like using a speaker and/or a haptic module. Further, the blood glucose estimating apparatus may determine a user's health condition based on the estimated blood glucose value, and may provide a warning or a response action based on the determination.

Figure 4:
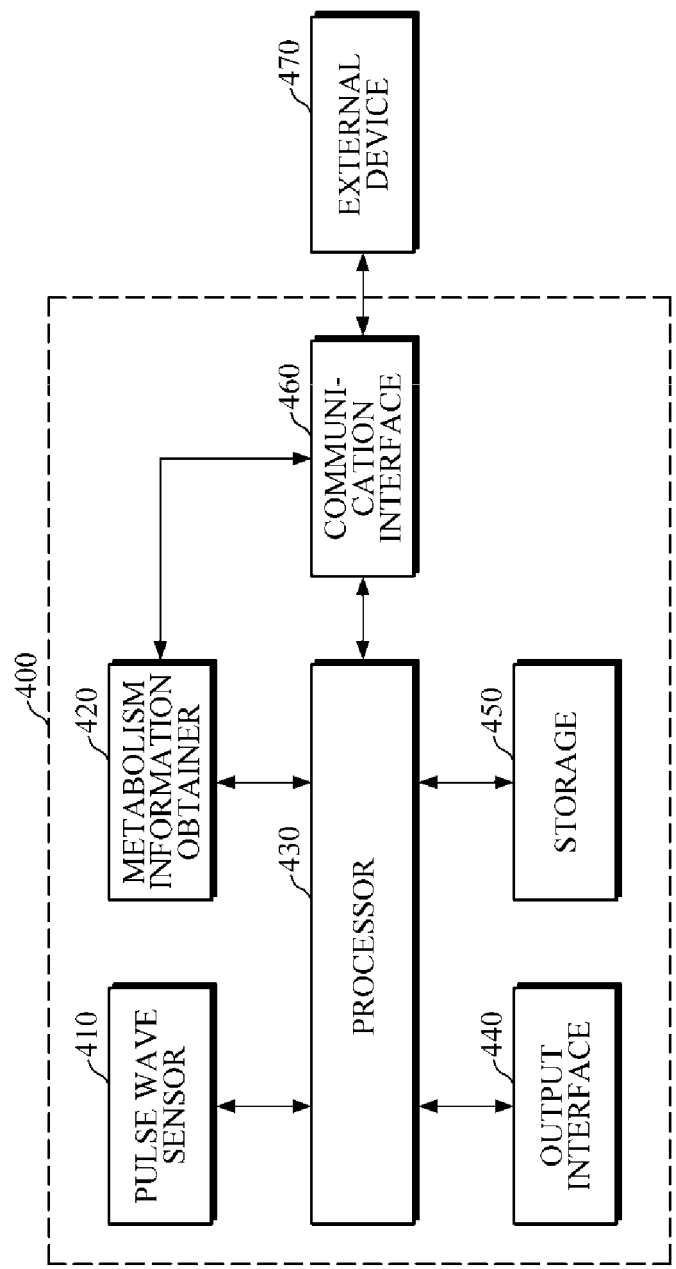
FIG. 4 is a block diagram illustrating an apparatus for estimating blood glucose according to another example embodiment.
Figure 5A:
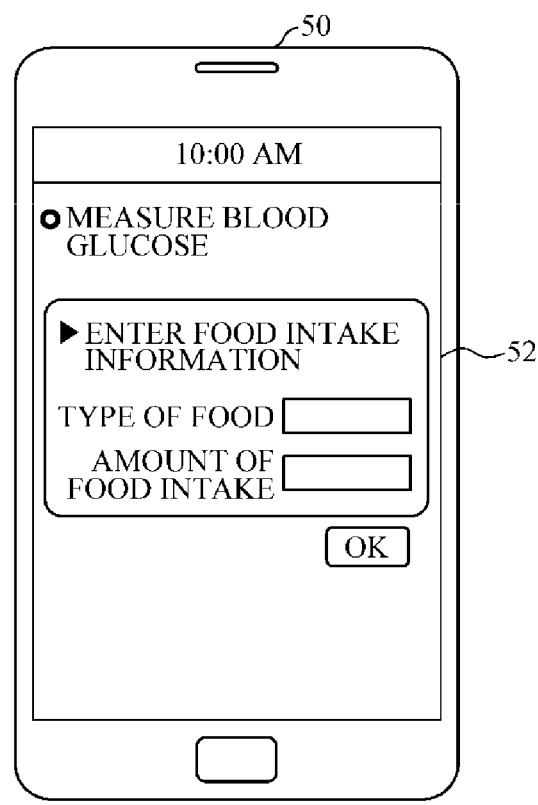
FIG. 5A is a diagram illustrating an example of an interface for obtaining metabolism information.
Figure 5B:
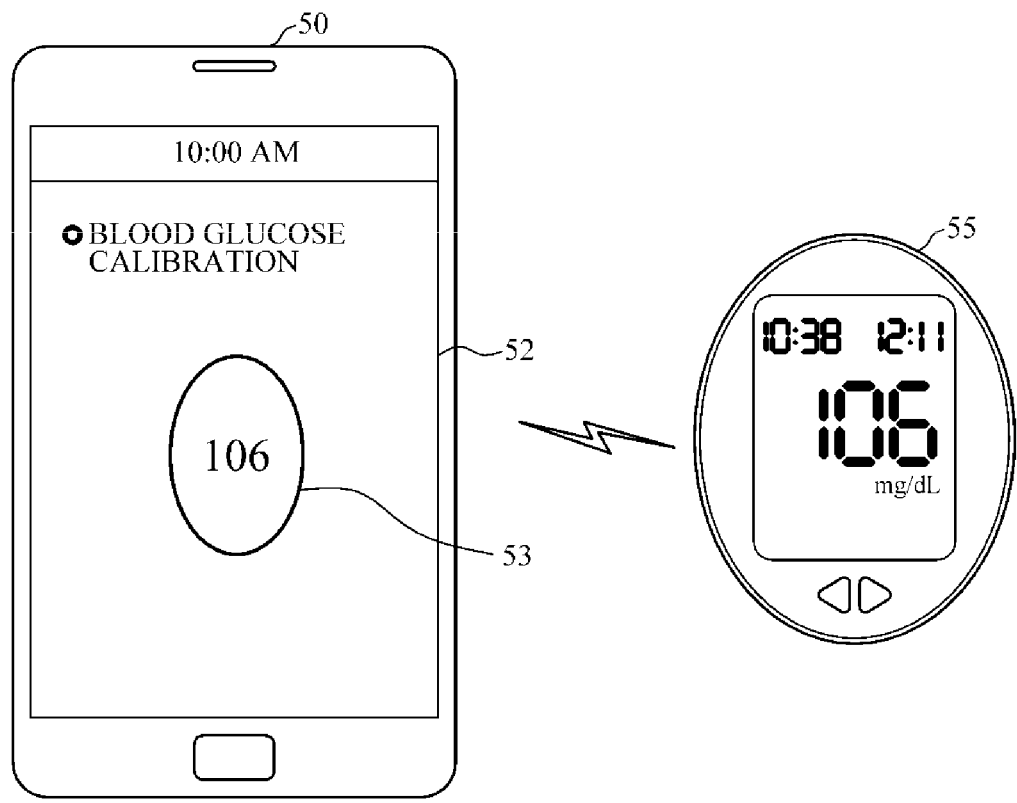
FIGS. 5B and 5C are diagrams illustrating examples of an interface for obtaining a calibration blood glucose value.
Figure 5C:
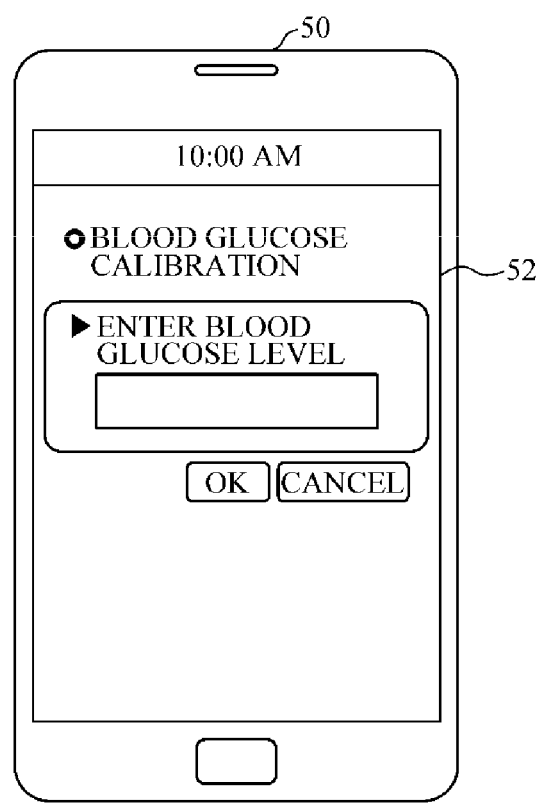

FIG. 4 is a block diagram illustrating an apparatus for estimating blood glucose according to another embodiment. FIG. 5A is a diagram illustrating an example of an interface for obtaining metabolism information. FIGS. 5B and 5C are diagrams illustrating examples of an interface for obtaining a calibration blood glucose value.

Referring to FIG. 4, the blood glucose estimating apparatus 400 according to an example embodiment includes a pulse wave sensor 410, a metabolism information obtainer 420, and a processor 430; and depending on an embodiment, may further include an output interface 440, a storage 450, and a communication interface 460.

The pulse wave sensor 410 may measure a pulse wave signal from an object, and may include one or more light sources which emit light onto the object, and a detector which detects light scattered or reflected from the object.

The metabolism information obtainer 420 may collect factors which affect blood glucose, for example, food intake information including consumed food, an amount of food intake, a time of food intake, and activity information including a time of insulin injection, exercise, sleep, and the like, and may obtain metabolism information based on the collected information. The food intake information and activity information are merely examples, such that the information is not limited thereto.

For example, as illustrated in FIG. 5A, the metabolism information obtainer 420 may output an interface for receiving input of food intake information from a user on a display 52 of an electronic device 50 in which the blood glucose estimating apparatus 400 is mounted, and may obtain food intake information input by a user. Further, the metabolism information obtainer 420 may output an interface for collecting a user's activity information, and may receive the activity information from a user.

In another example, the metabolism information obtainer 420 may obtain food intake information using a food intake sensor. In this case, the food intake sensor is a sensor which generates food intake sensor information by recognizing food intake by a user, and may be mounted in the blood glucose estimating apparatus 400 or may be manufactured as a separate hardware device to be attached or worn on a body part.

For example, the food intake sensor 120 may include a sensor which is worn on a user's ear to recognize the sound made by a user when consuming food; a gyro sensor which is worn on a user's wrist to recognize the motion of the arms; a sensor which recognizes the motion of the chest or respiration; a sensor for capturing an image of food consumed by a user; a piezoelectric sensor which recognizes a swallowing action of a user or a motion of the muscles in a user's throat. In addition, the food intake sensor 120 may include a camera module which obtains image information associated with food intake by a user, and the like. However, the food intake sensor 120 is not limited thereto.

Upon receiving the food intake sensor information, such as the sound of food intake, the captured image of food, the recognized swallowing action information, the recognized motion information of the arms, and the like, from the food intake sensor 120, the metabolism information obtainer 420 may analyze the received food intake sensor information, to obtain food intake information such as the types and amounts of food consumed by a user, and/or a food intake time.

In another example, the metabolism information obtainer 420 may obtain a slope change by analyzing continuous blood glucose measurements received from an invasive and/or minimally invasive or non-invasive blood glucose sensor, and may obtain food intake information based on the obtained slope change. For example, in the case where a slope of blood glucose levels suddenly changes in the continuous blood glucose measurements over a predetermined period of time, the metabolism information obtainer 420 may determine a point, at which the slope suddenly changes, as a time of food intake of a user. Further, the metabolism information obtainer 420 may estimate the types of food or an amount of food intake according to a change in blood glucose by using a model which is a predefined for each user and represents a correlation between a blood glucose change and food information.

However, the metabolism information obtainer 420 is not limited to these examples, and may recognize food intake information and/or activity information by using a slope change of the features of the pulse wave signal measured by the pulse wave sensor 410, or by combining information items obtained by various methods described above.

Upon obtaining the food intake information and/or activity information as described above, the metabolism information obtainer 420 may obtain metabolism information by using a predefined a state space metabolism model. In this case, the metabolism information may include a blood glucose variation, a blood glucose change rate over time, and a probability or frequency of blood glucose change stages, but is not limited thereto.

For example, the metabolism information obtainer 420 may obtain a blood glucose variation or a blood glucose change rate over time by applying a physiological metabolism model according to transfer of a substance, which is related to blood glucose, between body organs. For example, the metabolism model may be defined by formulating, as a linear or non-linear equation, blood glucose metabolism according to transfer of a substance between body organs (e.g., stomach, intestine, etc.). The metabolism model may be personalized by modeling various factors, associated with absorption of a substance in the body, distribution of a substance, metabolism by organs such as liver and stomach, excretion, and the like, for each user. However, the metabolism model is not limited thereto, and may be predefined in the form of a blood glucose database which represents a correlation between metabolism model information items such as food intake information and/or activity information, a blood glucose confidence interval over time, a probability or frequency of blood glucose change stages, and the like.

Once the pulse wave sensor 410 measures a pulse wave signal, the processor 430 may obtain features for estimating blood glucose from the pulse wave signal. For example, as described above, the processor 430 may obtain, as the feature, a difference between a time value at a peak point of the systolic interval and a time value at a peak point of the diastolic interval, or a time difference ratio obtained by dividing the difference by the time value at the peak point of the systolic interval. In this case, the processor 430 may detect local minimum points from a second order differential signal, which is obtained by performing second order differentiation on the pulse wave signal, and may obtain the peak point of the systolic interval and the peak point of the diastolic interval based on components of each constituent pulse waveform forming the pulse wave signal. However, the features are merely examples, and various other features may also be obtained.

Upon obtaining the features from the pulse wave signal, the processor 430 may obtain a first estimated blood glucose value by applying a first blood glucose estimation model. For example, the first blood glucose estimating model may be defines as a linear function which represents a correlation between a feature value and a blood glucose value as represented by the above Equation 1, but is not limited thereto.

Further, once the metabolism information obtainer 420 obtains metabolism information, the processor 430 may obtain a second estimated blood glucose value by applying a second blood glucose estimation model. The second blood glucose estimation model may be defined as a linear or non-linear function by using the metabolism information and a calibration blood glucose value. In this case, the calibration blood glucose value may refer to a blood glucose value measured by using an invasive and/or minimally invasive apparatus for measuring blood glucose at a calibration time, e.g., at a time of an empty stomach. The following Equation 2 is an example of a simple linear equation, but is not limited thereto.

$$y_2 = \alpha x_2 + \beta \qquad \text{[Equation 2]}$$

Here, $y_2$ denotes the second estimated blood glucose value obtained based on the metabolism information; $x_2$ denotes metabolism information, e.g., a blood glucose variation at a measurement time compared to a calibration time; and $\alpha$ and $\beta$ denote coefficients predefined through preprocessing. In this case, $\beta$ may be a calibration blood glucose value measured by using an invasive/minimally invasive apparatus for measuring blood glucose at a calibration time, e.g., at a time of an empty stomach.

Upon estimating the first estimated blood glucose value obtained using the pulse wave signal, and the second estimated blood glucose value obtained using the metabolism information, the processor 430 may estimate a final blood glucose value based on the first blood glucose value, the second blood glucose value, and a final blood glucose estimation model. The final blood glucose estimation model may be predefined based on weighted summation, Kalman Filter, regression, Artificial Intelligence, and the like. For example, the processor 430 may estimate a final blood glucose value by using a final blood glucose estimation model defined based on weighted summation as represented by the following Equation 3.

$$y = \omega_1 y_1 + \omega_2 y_2 \qquad \text{[Equation 3]}$$

Herein, $y_1$ and $y_2$ denote the first blood glucose value and the second blood glucose value respectively; $y$ denotes the final blood glucose value; and $\omega_1$ and $\omega_2$ denote weighted values applied to the first blood glucose value and the second blood glucose value respectively, in which the weighted values applied to the blood glucose values may be defined differently for each user. For example, in the case where a blood glucose value obtained by using a pulse wave signal of a specific user is relatively more accurate than a blood glucose value obtained by using metabolism information, i.e., is closer to an actual blood glucose value which is measured invasively, a weighted value to be applied to the first blood glucose value may be set to a higher value than a weighted value to be applied to the second blood glucose value for the user.

In addition, the final blood glucose estimation model may be defined by further considering a calibration blood glucose value which is measured at a calibration time, as represented by the following Equation 4. However, the final blood glucose estimation model is not limited thereto, and may be defined as various other modified models.

$$y = \omega_1 y_1 + \omega_2 y_2 + \omega_3 y_3 \quad \text{[Equation 4]}$$

Herein, $y_1$, $y_2$, and $y_3$ denote the first blood glucose value, the second blood glucose value, and the calibration blood glucose value, respectively; y denotes the final blood glucose value; and $\omega_1$, $\omega_2$, and $\omega_3$ denote weighted values applied to the first blood glucose value, the second blood glucose value, and the calibration blood glucose value, respectively.

Further, the processor 430 may determine whether to calibrate a blood glucose estimation model based on a blood glucose estimation result. For example, upon estimating the final blood glucose value, the processor 430 may check a calibration condition, and in response to the final blood glucose value satisfying the calibration condition, the processor 430 may calibrate a blood glucose estimation model. For example, the calibration condition may be defined as being satisfied in various cases, such as a case where a total number of times the estimated blood glucose values falling outside a normal range during a predetermined period of time is greater than or equal to a threshold value, a case where a number of times the estimated blood glucose values continuously falling outside a normal range is greater than or equal to a threshold value, or a case where the estimated blood glucose values deviate from a normal range by more than a predetermined threshold value.

Referring to FIG. 5B, in response to the calibration condition being satisfied, the processor 430 may control the communication interface 460 to be connected to an external blood glucose measuring device 55, and may control an output interface 440 to output on a display 52 visual information 53 indicating that connection to the blood glucose measuring device 55 has been made. In this case, the visual information may include a visual object, such as an image of the blood glucose measuring device 55, and/or a measured blood glucose value.

Referring to FIG. 5C, in the case where connection to an external blood glucose measuring device is impossible, or in response to a user's request, the processor 430 may output an interface for receiving a calibration blood glucose value directly from a user on the display 52 of an electronic device 50.

Upon receiving input of the calibration blood glucose value as described above, the processor 430 may calibrate a blood glucose estimation model based on the input calibration blood glucose value.

In addition, as described above, the output interface 440 may output a processing result of the processor 430 and various types of information obtained by the pulse wave sensor 410 or the metabolism information obtainer 420 by various visual or non-visual methods. Further, the output interface 440 may output an interface for receiving food intake information or a calibration blood glucose value from a user. In the case where the communication interface 460 is connected to the external device 470, the output interface 440 may output a connection state, information received from the external device 470, and the like.

The storage 450 may store various information such as the pulse wave signal measured by the pulse wave sensor 410, the food intake information, activity information, and metabolism information obtained by the metabolism information obtainer 420, and/or a processing result of the processor 430. Further, the storage 450 may store various types of reference information to be used for estimating blood glucose, e.g., a first blood glucose estimation model, a second blood glucose estimation model, and a third blood glucose estimation model. In addition, the storage 450 may store a calibration blood glucose value or a user's personal information. However, the storage 450 is not limited thereto, and may store various other types of information.

The communication interface 460 may communicate with various external devices, including an external blood glucose measuring device, by using communication techniques to transmit and receive various types of information. For example, the communication interface 460 may transmit a blood glucose estimation result of the processor 430 to a user's information processing device, e.g., a desktop computer or a laptop computer, which has a relatively high computing performance, for use in monitoring comprehensive health management of a user. Alternatively, the communication interface 460 may receive a blood glucose estimation model from an external device, which generates a blood glucose estimation model based on information of a plurality of users.

Figure 6:
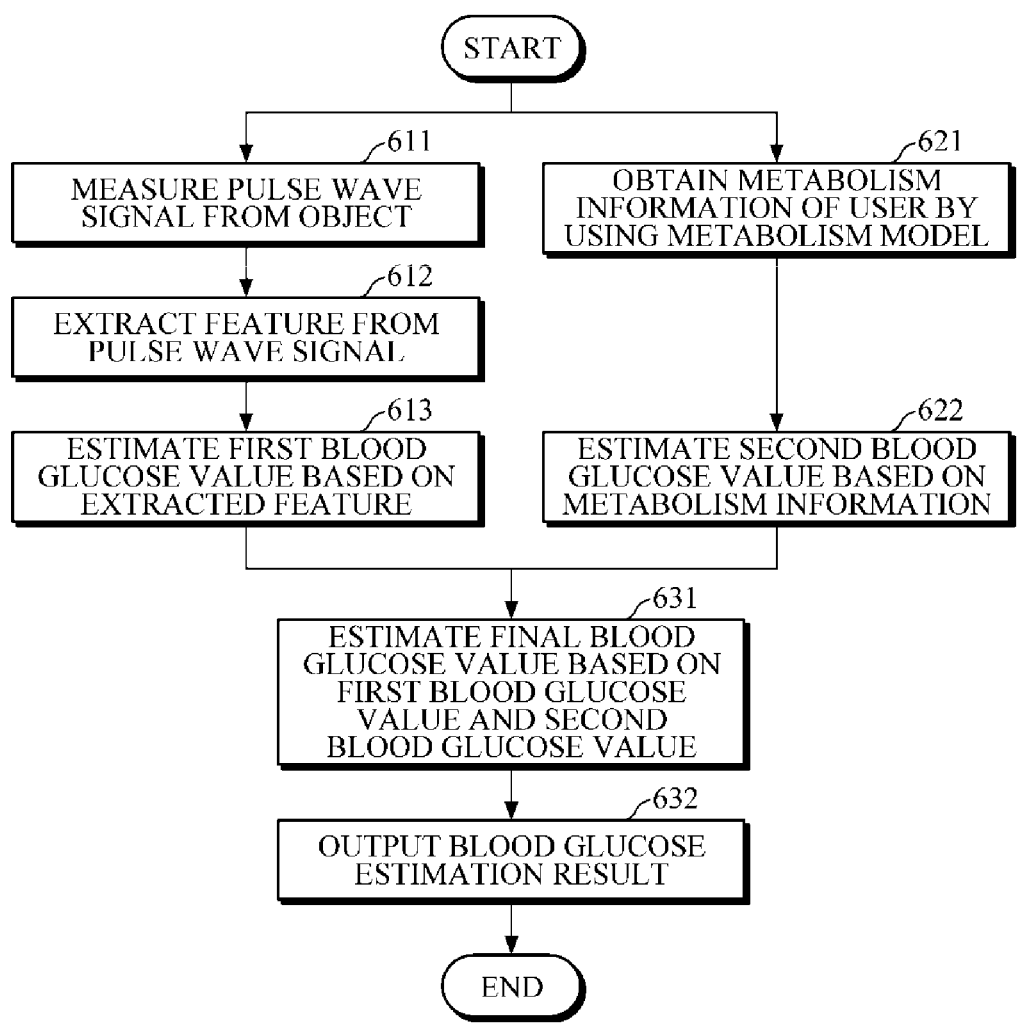
FIG. 6 is a flowchart illustrating a method of estimating blood glucose according to another embodiment.

FIG. 6 is a flowchart illustrating a method of estimating blood glucose according to another embodiment. The blood glucose estimating method of FIG. 6 may be performed by the blood glucose estimating apparatus 400 of FIG. 4, which will be described briefly below to avoid redundancy.

The blood glucose estimating apparatus 400 may measure a pulse wave signal from an object in 611, and may extract features from the measured pulse wave signal based on time information at two or more points in 612. For example, the blood glucose estimating apparatus 400 may extract features based on time values of a peak of the systolic interval and a peak of the diastolic interval of the pulse wave signal.

The blood glucose estimating apparatus 400 may estimate a first blood glucose value based on the extracted features in 613. For example, the blood glucose estimating apparatus 400 may obtain the first blood glucose value by inputting the extracted feature value to a predefined first blood glucose estimation model.

Subsequently, the blood glucose estimating apparatus 400 may obtain metabolism information of a user by using a metabolism model in 621, and may estimate a second blood glucose value based on the obtained metabolism information in 622. For example, the blood glucose estimating apparatus 400 may collect food intake information associated with food consumed by a user during a predetermined period of time, or activity information of a user, and may obtain metabolism information based on the collected food intake information and/or activity information. In this case, the operations 621 and 622 may be performed during, prior to, or subsequent to the operations 611 to 613.

Next, the blood glucose estimating apparatus 400 may estimate a final blood glucose value based on the first blood glucose value and the second blood glucose value in 631. In this case, the blood glucose estimating apparatus 400 may estimate the final blood glucose value by using a predefined final blood glucose estimation model as represented by the above Equation 3 or 4.

The blood glucose estimating apparatus may output a blood glucose estimation result and provide the result for a user in 632. For example, the blood glucose estimating apparatus may output the blood glucose estimation result by various visual methods using a visual output device such as a display module and the like. Alternatively, the blood glucose estimating apparatus may provide a user with the blood glucose estimation result by a non-visual method through voice, tactile sensation, vibrations, and the like using a speaker module and/or a haptic module. Further, the blood glucose estimating apparatus may determine a user's health condition based on the estimated blood glucose value, and may provide a warning or a response action for a user based on the determination.

According to an example embodiment, the apparatus for estimating blood glucose may obtain a more accurate blood glucose estimation value by further considering a blood glucose value, which is estimated using a metabolism model, in addition to a blood glucose value estimated using a PPG signal.

The example embodiments can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the example embodiments can be easily deduced by one of ordinary skill in the art.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

While a few example embodiments have been described above, the scope of the disclosure is not limited thereto and various modifications and improvements made by those of ordinary skill in the art to concepts defined in the following claims should be understood to fall within the scope of the disclosure.

What is claimed is:

1. An apparatus for estimating blood glucose, the apparatus comprising:
   a pulse wave sensor configured to obtain a pulse wave signal from an object;
   a processor configured to:
      detect a first local minimum point and a second local minimum point from a second order differential signal, obtained by performing second order differentiation on the pulse wave signal;
      obtain a first point in a systolic interval of the pulse wave signal corresponding to the first local minimum point, and obtain a second point in a diastolic interval of the pulse wave signal corresponding to the second local minimum point;
      extract, as a feature, a difference between a time value of the first point and a time value of the second point;
      estimate a first blood glucose value by applying a blood glucose estimation model to the extracted feature,
      estimate a final blood glucose value based on a weighted summation between the first blood glucose value that is estimated based on the extracted feature and a calibration blood glucose value which is measured at a calibration time, and
   an output interface configured to provide the estimated final blood glucose value,
   wherein the processor is further configured to, based on the estimated final blood glucose value satisfying a calibration condition, calibrate the blood glucose estimation model, the calibration condition comprising at least one of a condition that a total number of times the estimated final blood glucose value falling outside a normal range during a predetermined period of time is greater than or equal to a first threshold value, a condition that a number of times the estimated final blood glucose value continuously falling outside the normal range is greater than or equal to a second threshold value, or a condition that the estimated final blood glucose value deviates from the normal range by more than a third threshold value, and
   wherein the processor is further configured to, based on the estimated final blood glucose value satisfying the calibration condition, control the output interface to display (i) information related to a blood glucose measuring device that is connected with the apparatus and/or (ii) an interface for receiving a new calibration blood glucose value from a user.

2. The apparatus of claim 1, wherein the pulse wave sensor comprises:
   at least one light source configured to emit light of at least one wavelength onto the object; and
   at least one detector configured to detect the light of the at least one wavelength that is scattered or reflected from the object.

3. The apparatus of claim 2, wherein the at least one wavelength comprise at least one of a red wavelength, a green wavelength, a blue wavelength, and an infrared wavelength.

4. The apparatus of claim 1, wherein the processor is further configured to extract, as the feature, a time difference ratio obtained by dividing the difference by the time value of the first point or the time value of the second point.

5. The apparatus of claim 1, wherein the processor is further configured to obtain a component of a pulse waveform forming a waveform of the pulse wave signal, and obtain the first point and the second point based on the obtained component of the pulse waveform.

6. The apparatus of claim 1, wherein the feature comprises at least one of pulse rate variability, heart rate variability, heart rate, pulse rate, arterial stiffness, blood pressure, perfusion index, and pulsatile volume.

7. A method of estimating blood glucose, the method comprising:
- obtaining, by using a pulse wave sensor, a pulse wave signal from an object;
- detecting a first local minimum point and a second local minimum point from a second order differential signal, obtained by performing second order differentiation on the pulse wave signal;
- obtaining a first point in a systolic interval of the pulse wave signal corresponding to the first local minimum point, and obtaining a second point in a diastolic interval of the pulse wave signal corresponding to the second local minimum point;
- extracting, as a feature, a difference between a time value of the first point and a time value of the second point;
- estimating a first blood glucose value by applying a blood glucose estimation model to the extracted feature;
- estimating a final blood glucose value based on a weighted summation between the first blood glucose value that is estimated based on the extracted feature and a calibration blood glucose value which is measured at a calibration time;
- outputting, via an output interface, the estimated final blood glucose value;
- based on the estimated final blood glucose value satisfying a calibration condition, calibrating the blood glucose estimation model, the calibration condition comprising at least one of a condition that a total number of times the estimated final blood glucose value falling outside a normal range during a predetermined period of time is greater than or equal to a first threshold value, a condition that a number of times the estimated final blood glucose value continuously falling outside the normal range is greater than or equal to a second threshold value, or a condition that the estimated final blood glucose value deviates from the normal range by more than a third threshold value; and
- based on the estimated final blood glucose value satisfying the calibration condition, controlling the output interface to display (i) information related to a blood glucose measuring device that is connected with an apparatus for estimating blood glucose and/or (ii) an interface for receiving a new calibration blood glucose value from a user.

8. The method of claim 7, wherein the extracting comprises extracting, as the feature, a time difference ratio obtained by dividing the difference by the time value of the first point or the time value of the second point.

9. The method of claim 7, wherein the obtaining the first point and the second point further comprises obtaining a component of a pulse waveform forming a waveform of the pulse wave signal, and obtaining the first point and the second point based on the obtained component of the pulse waveform.

10. An apparatus for estimating blood glucose, the apparatus comprising:
- a pulse wave sensor configured to obtain a pulse wave signal from an object;
- a processor configured to:
  - detect a first local minimum point and a second local minimum point from a second order differential signal, obtained by performing second order differentiation on the pulse wave signal;
  - obtain a first point in a systolic interval of the pulse wave signal corresponding to the first local minimum point, and obtain a second point in a diastolic interval of the pulse wave signal corresponding to the second local minimum point;
  - extract, as a feature, a difference between a time value of the first point and a time value of the second point; and
  - estimate a first blood glucose value by applying a blood glucose estimation model to the extracted feature;
- a metabolism information obtainer configured to obtain metabolism information of a user; and
- an output interface,
- wherein the processor is further configured to estimate a second blood glucose value based on the metabolism information, and to estimate a final blood glucose value based on a weighted summation between the first blood glucose value, the second blood glucose value, and a calibration blood glucose value which is measured at a calibration time, and
- wherein the output interface is configured to provide the estimated final blood glucose value,
- wherein the processor is further configured to, based on the estimated final blood glucose value satisfying a calibration condition, calibrate the blood glucose estimation model, the calibration condition comprising at least one of a condition that a total number of times the estimated final blood glucose value falling outside a normal range during a predetermined period of time is greater than or equal to a first threshold value, a condition that a number of times the estimated final blood glucose value continuously falling outside the normal range is greater than or equal to a second threshold value, or a condition that the estimated final blood glucose value deviates from the normal range by more than a third threshold value, and
- wherein the processor is further configured to, based on the estimated final blood glucose value satisfying the calibration condition, control the output interface to display (i) information related to a blood glucose measuring device that is connected with the apparatus and/or (ii) an interface for receiving a new calibration blood glucose value from the user.

11. The apparatus of claim 10, wherein the processor is further configured to:
- extract, as the feature, a time difference ratio obtained by dividing the difference by the time value of the first point or the time value of the second point.

12. The apparatus of claim 11, wherein the processor is further configured to obtain a component of a pulse waveform forming a waveform of the pulse wave signal, and obtain the first point and the second point based on the obtained component of the pulse waveform.

13. The apparatus of claim 10, wherein the metabolism information obtainer is further configured to obtain the metabolism information based on at least one of sensor information and user input information, the sensor information being received from at least one of the pulse wave sensor, a food intake sensor, and a blood glucose sensor.

14. The apparatus of claim 13, wherein the metabolism information obtainer is further configured to obtain the metabolism information by applying at least one of the sensor information and the user input information to a metabolism model.

15. The apparatus of claim 13, wherein the metabolism information comprises at least one of a blood glucose change rate over time, a blood glucose variation, and a probability or a frequency of stages of blood glucose change.

16. The apparatus of claim 10, wherein the calibration blood glucose value is obtained by a blood glucose sensor.

17. A method of estimating blood glucose, the method comprising:
    obtaining, by using a pulse wave sensor, a pulse wave signal from an object;
    detecting a first local minimum point and a second local minimum point from a second order differential signal, obtained by performing second order differentiation on the pulse wave signal;
    obtaining a first point in a systolic interval of the pulse wave signal corresponding to the first local minimum point, and obtaining a second point in a diastolic interval of the pulse wave signal corresponding to the second local minimum point;
    extracting, as a feature, a difference between a time value of the first point and a time value of the second point;
    estimating a first blood glucose value by applying a blood glucose estimation model to the extracted feature;
    obtaining metabolism information of a user, and estimating a second blood glucose value based on metabolism information;
    estimating a final blood glucose value based on a weighted summation between the first blood glucose value, the second blood glucose value, and a calibration blood glucose value which is measured at a calibration time;
    outputting, via an output interface, the estimated final blood glucose value;
    based on the estimated final blood glucose value satisfying a calibration condition, calibrating the blood glucose estimation model, the calibration condition comprising at least one of a condition that a total number of times the estimated final blood glucose value falling outside a normal range during a predetermined period of time is greater than or equal to a first threshold value, a condition that a number of times the estimated final blood glucose values continuously falling outside the normal range is greater than or equal to a second threshold value, or a condition that the estimated final blood glucose value deviates from the normal range by more than a third threshold value; and
    based on the estimated final blood glucose value satisfying the calibration condition, controlling the output interface to display (i) information related to a blood glucose measuring device that is connected with an apparatus for estimating blood glucose and/or (ii) an interface for receiving a new calibration blood glucose value from the user.

18. The method of claim 17, wherein the extracting comprises:
    extracting, as the feature, a time difference ratio obtained by dividing the difference by the time value of the first point or the time value of the second point.

19. The method of claim 17, wherein the obtaining the metabolism information comprises obtaining the metabolism information based on at least one of sensor information and user input information, the sensor information being received from at least one of the pulse wave sensor, a food intake sensor, and a blood glucose sensor.

20. The method of claim 19, wherein the obtaining the metabolism information comprises obtaining the metabolism information by applying at least one of the sensor information and the user input information to a metabolism model.

* * * * *